(12) United States Patent
Wu et al.

(10) Patent No.: US 6,398,707 B1
(45) Date of Patent: Jun. 4, 2002

(54) METHOD OF PREPARING LOWER ALKYL FATTY ACIDS ESTERS AND IN PARTICULAR BIODIESEL

(75) Inventors: Wen-Teng Wu, Department of Chemical Engineering, National Tsing Hua University, Hsinchu (TW), 300; Jech-Wei Chen, Hsinchu (TW)

(73) Assignee: Wen-Teng Wu, Hsinchu (TW)

( * ) Notice: Subject to any disclaimer, the term of this patent is extended or adjusted under 35 U.S.C. 154(b) by 0 days.

(21) Appl. No.: 09/867,674

(22) Filed: May 31, 2001

(51) Int. Cl.[7] ............................................. C11C 3/00
(52) U.S. Cl. ..................... 584/169; 435/132; 435/134; 435/135
(58) Field of Search .................. 584/169; 435/132, 435/134, 135

(56) References Cited

PUBLICATIONS

Matsumoto et al., Journal of Chem. Technol. Biotechnol., vol. 76, pp. 1070–1073, Sep. 2001.*

Yomi Watanabe, Yuji Shimada, Akio Sugihara, Hideo Noda, Hideki Fukuda and Yoshio Tominaga, Continuous Production of Biodiesel Fuel From Vegetable Oil Using Immobilized Candida antarctica Lipase, JAOCS, vol. 77, pp. 355–360, 2000.

Kobori Satoru, Arakawa Hiroshi and Hirokawa Toshiyuki, Reactivation of Immobilized Lipase, Japanese Patnet Application Publication No. 11–75834, Mar. 23, 1999 (Abstract).

* cited by examiner

*Primary Examiner*—Deborah D Carr
(74) *Attorney, Agent, or Firm*—Bacon & Thomas, PLLC

(57) ABSTRACT

The present invention relates to a technique for enhancing the activity of an immobilized lipase, and a technique for regenerating a deactivated immobilized lipase, in which an alcohol with a carbon atom number not less than three is used to swell and/or clean said immobilized lipase. Said immobilized lipase is particularly useful in a method of preparing biodiesel by transesterification of triglycerides and a lower alcohol.

18 Claims, 4 Drawing Sheets

METHOD OF PREPARING LOWER ALKYL FATTY ACIDS ESTERS AND IN PARTICULAR BIODIESEL

FILED OF THE INVENTION

The present invention relates to techniques for improving the activity of an immobilized lipase and for regenerating a deactivated immobilized lipase, wherein said immobilized lipase is particularly useful in a method of generating biodiesel by transesterification of triglycerides and a lower alcohol.

BACKGROUND OF THE INVENTION

In many countries, e.g. Europe, U.S.A., and Japan, etc., strong bases have been used as a catalyst in industrial processes for producing biodiesel, for example U.S. Pat. No. 5,354,878. Such industrial processes have a production scale of hundreds of thousands of tons. Even so, a strong base process suffers some serious defects. For example, a strong base process can not smoothly handle rendered oils and fats which contain a higher content of impurities. The impurities described herein mainly are moisture and free fatty acids commonly contained in rendered feedstock oils, rendered animal fats, and rendered oils and rendered fats generated in the refining of feedstock oils. The existence of these impurities will cause a strong base process to generate many undesirable by-products (e.g. soap), thereby lowering the yield of biodiesel and making purification of the biodiesel product more difficult. Therefore, nearly all commercial strong base processes for producing biodiesel use pure vegetable oils as the raw material.

At present, there are two major key difficulties in using lipase to produce biodiesel. The first difficulty is that the activity of lipase is relatively low. In an article presented by Watanabe, et al., ["Continuous Production of Biodiesel Fuel from Vegetable Oil Using Immobilized *Candida antarctica* Lipase", JAOCS, vol. 77, pp. 355–360, 2000], the lipase process requires 36 hours to complete the reaction which is significantly longer than one hour required by the strong base process. Another difficulty is that the price of lipase is much higher than the price of sodium hydroxide (NaOH) used by the strong base process. Unless an immobilized lipase having an enhanced activity is used, and the activity of the immobilized lipase can be maintained after being recycled for a certain number of times, a lipase process is difficult to compete with the strong base process in terms of the production cost. Unfortunately, the immobilized lipase is liable to be poisoned by a lower alcohol, and the deactivated immobilized lipase can not be regenerated effectively with its recovered activity being comparable to that of the parent immobilized lipase. Therefore, in order to make an immobilized lipase process becoming economically feasible, or even replacing the conventional strong base process, issues such as how to increase the activity and life-span of an immobilized lipase, and how to effectively regenerate an immobilized lipase that is partially or completely deactivated, have become very important.

One objective of the present invention is to provide a method suitable for enhancing the activity of an immobilized lipase.

Another objective of the present invention is to provide a method for regenerating an immobilized lipase having a reduced activity.

Still another objective of the present invention is to provide a method of preparing a lower alkyl fatty acid ester, in particular biodiesel, by transesterification or esterification of a fatty acid glyceride or a free fatty acid with a lower alcohol using a pretreated or regenerated immobilized lipase as the catalyst.

SUMMARY OF THE INVENTION

The inventors of the present invention deem that a decrease in the activity of transesterification of a fatty acid glyceride and a lower alcohol is mainly caused by physical factors, i.e. the immiscibility between methanol or ethanol and fatty acid glycerides. Consequently, when methanol or ethanol is absorbed into the voids of an immobilized lipase, the entry of fatty acid glyceride into the voids will be blocked, stopping the reaction from taking place. The inventors also observe that methanol is easier to be absorbed by the immobilized lipase than an oil. The inventors of the present invention first disclose an ideal solvent to wash a deactivated immobilized lipase. This solvent needs to be harmless to the lipase, and has a good solubility to oil, grease, moisture, and methanol or ethanol. For example, an alcohol with three or more than three carbon atoms, preferably iso-propanol, 2-butanol and tert-butanol, can effectively regenerate a deactivated immobilized lipase. The inventors also discover that the activity of an immobilized lipase can be significantly increased when such an ideal solvent is used to perform an immersion pretreatment on an immobilized lipase.

In a preferred embodiment of the present invention, the activity of a commercially available immobilized lipase Novozyme 435 was increased 8–10 times in comparison with the one receiving no pretreatment; and a deactivated Novozyme 435 was successfully regenerated to an activity level equivalent to the level before being poisoned.

DETAILED DESCRIPTION OF THE INVENTION

Figure 1:
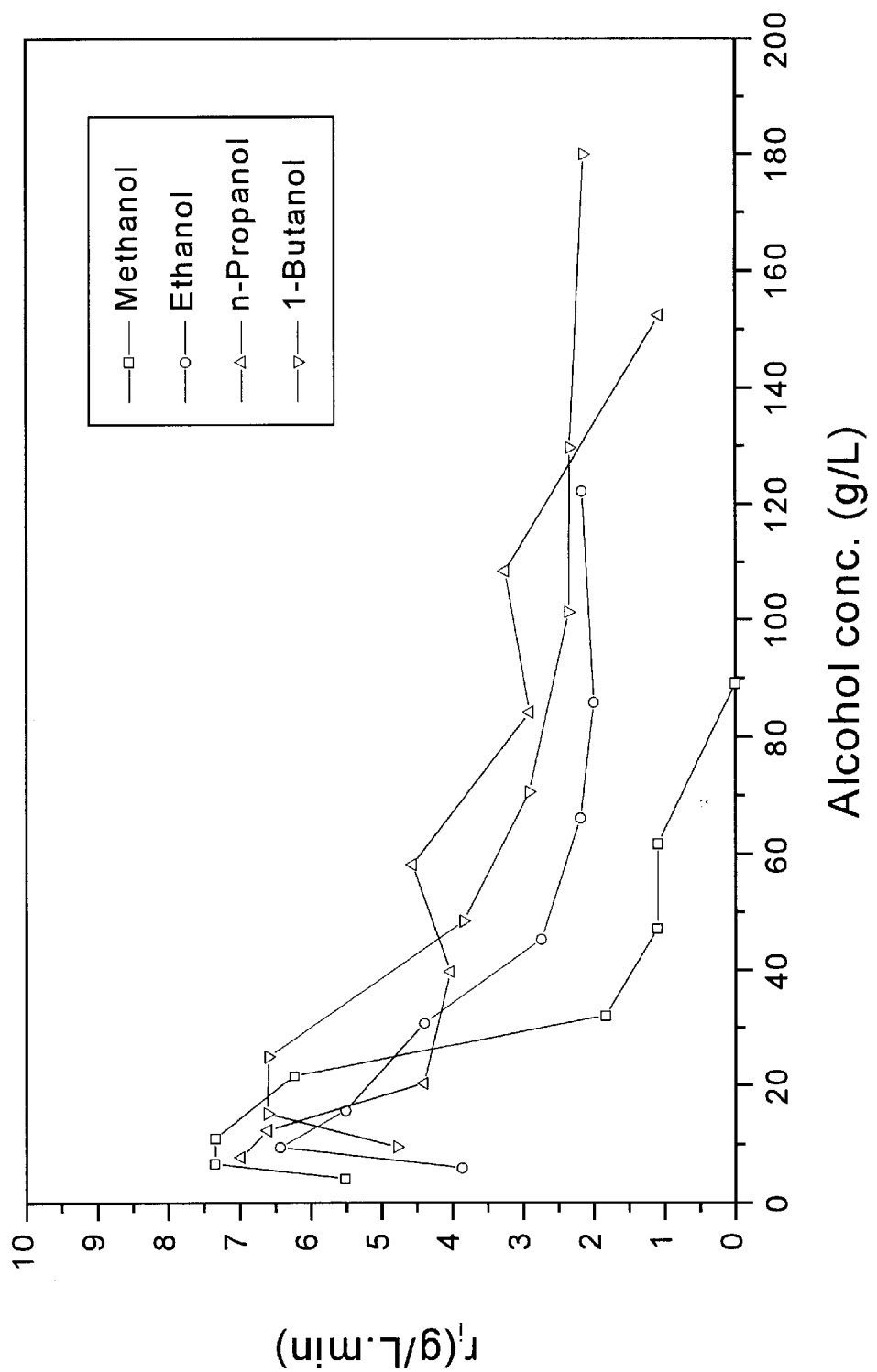
FIG. 1 shows the initial reaction rate of a known transesterification reaction versus the concentration of various linear alcohols, wherein a square represents methanol, a circle represents ethanol, a triangle represents n-propanol, and an inverted triangle represents 1-butanol.

The present invention provides a method of preparing a $C_1$–$C_3$ alkyl ester of a fatty acid by transesterification or esterification of a fatty acid glyceride or a free fatty acid with a $C_1$–$C_3$ alcohol, characterized in that a pretreated immobilized lipase is used to catalyze the transesterification or esterification, wherein said pretreated immobilized lipase is prepared by immersing an immobilized lipase in an alcohol having a carbon atom number not less than 3 for a period of time, preferably from 0.5–48 hours, and more preferably from 0.5–1.5 hours.

Preferably, said alcohol having a carbon atom number not less than 3 has a carbon atom number of 3–8, and more preferably 3 or 4, for examples 1-propanol, iso-propanol, 1-butanol, 2-butanol, iso-butanol or tert-butanol.

Preferably, said pretreated immobilized lipase is prepared by further immersing said immobilized lipase in a vegetable oil for 0.5–48 hours after removing said immobilized lipase from said alcohol having a carbon atom number not less than 3.

Preferably, said immobilized lipase is immobilized on a porous support.

Preferably said immobilized lipase is from Pseudomanas or Candida.

In the method of the present invention, said immobilized lipase can be fresh or deactivated.

In a case where said immobilized lipase is a deactivated immobilized lipase, said pretreated immobilized lipase is prepared by washing said deactivated immobilized lipase with the alcohol having a carbon atom number not less than 3. Preferably, said pretreated immobilized lipase is prepared by further immersing said deactivated immobilized lipase in a vegetable oil for 0.5–48 hours after washing said deactivated immobilized lipase with said alcohol having a carbon atom number not less than 3.

Preferably, said $C_1$–$C_3$ alkyl ester is prepared by transesterification of said fatty acid glyceride and said $C_1$–$C_3$ alcohol. More preferably, said $C_1$–$C_3$ alkyl ester is methyl ester, and said methyl ester is prepared by the transesterification of methanol and an oil or grease comprising a triglyceride, for example a vegetable oil.

Preferably, said $C_1$–$C_3$ alkyl ester is prepared by transesterification of said fatty acid glyceride and said $C_1$–$C_3$ alcohol, and the esterification of said free fatty acid and said $C_1$–$C_3$ alcohol. More preferably, said $C_1$–$C_3$ alkyl ester is methyl ester, and said methyl ester is prepared by the transesterification and esterification of methanol and an oil or grease comprising a glyceride and a free fatty acid. said oil or grease may be a vegetable oil, an animal grease, a recycled rendered feedstock oils, or a rendered oil or grease generated during the refining of feedstock oils.

Immobilized lipase applicable in the present invention is not specifically limited and can be those disclosed in the prior art, e.g. U.S. Pat. Nos. 4,798,793; 4,940,845 5,156, 963; 5,342,768; 5,776,741 and WO89/01032.

The transesterification reaction or esterification reaction of a fatty acid glyceride or a free fatty acid and a lower alcohol catalyzed by an immobilized lipase in order to prepare lower alkyl fatty acid esters, including biodiesel, was known by the people skilled in the art, and is not a key feature of the present invention. Therefore, the reactions will be not elaborated in details herein. According to the present invention, preferable conditions of the transesterification reaction or the esterification reaction are a temperature between the room temperature and 80° C., and a mole ratio of the fatty acid glyceride or free fatty acid to the lower alcohol of greater than 1:1, preferably about 3:1.

Figure 2:
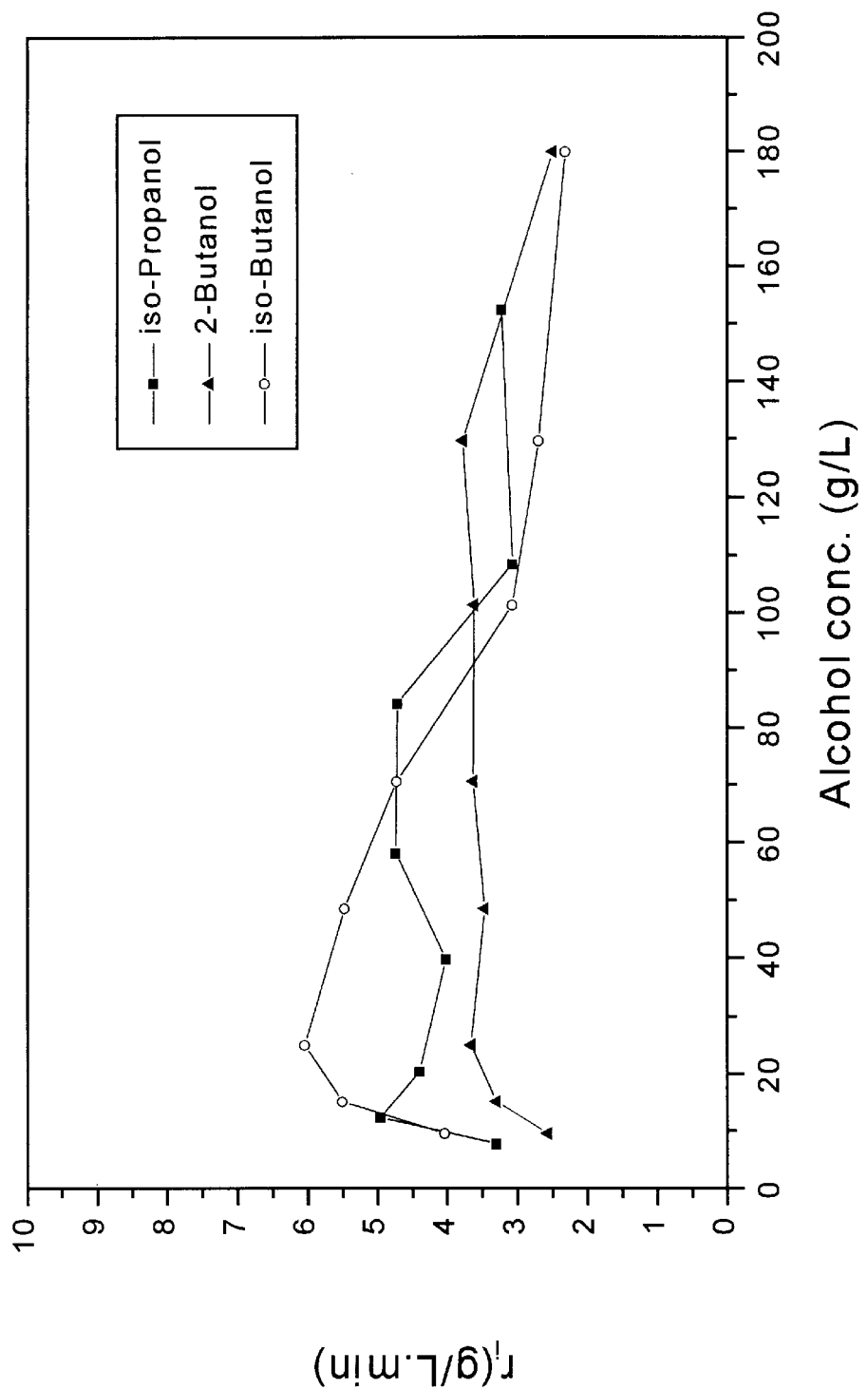
FIG. 2 shows the initial reaction rate of a known transesterification reaction versus the concentration of various branched alcohols, wherein a square represents iso-propanol, a triangle represents 2-butanol, and a circle represents iso-butanol.

The present invention first investigated the effect of various alcohols such as methanol, ethanol, n-propanol, 1-butanol, 2-butanol, iso-butyl alcohol, and tertbutanol, on the activity of an immobilized lipase. A fixed amount of a vegetable oil (5.7 g, soybean oil from the Taiwan Sugar Corp.) was mixed with an alcohol at different mole ratios (oil:alcohol=8:1, 5:1, 3:1, 3:2, 1:1, 2:3, 1:2, 1:3), and then added with 5 weight % (based on the weight of oil) of an immobilized lipase (Novozyme 435, produced by the Novo Nordisk Co., Denmark), wherein the lipase was immersed in oil in advance for 24 hours. The reaction was carried out in a test tube with a cap, in an incubating chamber at 30° C., at an oscillation rate of 200 rpm, for 5 minutes. After the reaction, the sample was analyzed by HPLC for the contents of biodiesel and unreacted oil. The initial reaction rate of the immobilized lipase was calculated as an index for the activity thereof. The results are shown in FIG. 1 and FIG. 2. All linear lower alcohols (methanol, ethanol, propanol, and butanol) are conspicuously poisonous to the immobilized lipase with variation in strength, as shown in FIG. 1. The strength of poisoning is inversely proportional to the number of carbon atoms of the linear lower alcohol. An alcohol having a higher number of carbon atoms is less poisonous to the immobilized lipase. FIG. 2 shows the poisoning strength of branched alcohols to an immobilized lipase. It can be seen from FIG. 2 that the strength of poisoning of a branched alcohol is lower than that of a linear alcohol. Particularly, the curves of iso-propanol and 2-butanol are almost horizontal, i.e., iso-propanol and 2-butanol have no obvious toxicity. Furthermore, tert-butanol, regardless at what concentration, can not form bonding with fatty acid glycerides in the presence of the immobilized lipase Novozyme 435, with a conversion of zero.

Two important discoveries were found in the above experiments. Firstly, when the Novozyme 435 was poisoned by methanol or ethanol, the particles of Novozyme 435 underwent a conspicuous change in appearance, and changed from the original transparent golden color to an opaque gray color, accompanied by swelling and caking of the particles. Secondly, methanol and ethanol had a poor miscibility with a vegetable oil. When more than one ninth of the theoretical mole number of a lower alcohol (methanol or ethanol) (alcohol:oil>1:3) was added to the oil, the resulting mixture turned into an emulsion state. The concentration of the lower alcohol at which the emulsion state occurs was nearly the same as the concentration causing poisoning of the immobilized lipase. A higher alcohol had a better miscibility with an oil. An alcohol with a carbon atom number exceeding three was completely miscible with a vegetable oil at least at a concentration below the theoretical mole ratio required in the transesterification of a triglyceride (alcohol:oil≦3:1).

Based on the above-mentioned two discoveries, iso-propanol and 2-butanol, that had no obvious toxicity to the Novozyme 435, and tert-butanol, that was inert to the fatty acid glyceride, were used to carry out an immersion pretreatment on the Novozyme 435 in the following examples. The results indicate that the immersion pretreatment not only is not poisonous to the immobilized lipase, but also, under certain circumstances, increases the resistance of the immobilized lipase to the poisoning of methanol and ethanol. Furthermore, the use of iso-propanol to wash a deactivated Novozyme 435 can also resume the activity of the deactivated Novozyme 435.

EXAMPLE 1

Effect of Pretreatment on the Activity of the Immobilized Lipase 0.3 g of Novozyme 435 immobilized lipase (purchased from Novo Nordisk Co., Denmark) was placed in a test tube and capped, and then immersed in different solvents (soybean oil, biodiesel, iso-propanol, 2-butanol, tert-butanol, and n-hexane) to enable swelling of the lipase particles, or without immersion as a control. The immersion conditions are shown in Table 1. Each of the immersed lipases and the control lipase was added with 5.7 g of soybean oil and 0.26 ml of methanol to carry out the reaction in an incubating chamber at 30° C. under oscillation of 200 rpm for 30 minutes. Upon completion of the reaction, 0.1 g of the sample was taken, and diluted with 10 ml of n-hexane, and then analyzed by HPLC to obtain the contents of the methyl ester and unreacted oil. The results are shown in Table 1. The results of Table 1 show that the pretreatment is very important to the immobilized lipase. When the lipase is immersed by a non-toxic alcohol (iso-propanol, 2-butanol, tert-butanol), the yield of methyl ester is about seven times of that of an immobilized lipase that is not pretreated. The immersion in a non-toxic alcohol has a better effect than the immersion in biodiesel, wherein the activity of the immobilized lipase pretreated by the former is 40% higher than the latter. When n-hexane is used in the immersion pretreatment, the activity of the pretreated immobilized lipase is close to that of an immobilized lipase that receives no pretreatment. This indicates that n-hexane has a high toxicity to Novozyme 435. When an immobilized lipase was pretreated according to the present invention, not only the initial activity of the pretreated immobilized lipase is increased significantly, but also the pretreated lipase has a higher resistance to the toxicity of methanol, as shown in the following example.

TABLE 1

Effect of pretreatment on reaction activity

| Type of pretreatment | Yield of methyl ester (%) |
|---|---|
| None | 2.5 |
| Oil 4 hr | 8.6 |
| Oil overnight | 10.0 |
| Biodiesel 0.5 hr + Oil 4 hr | 4.1 |
| Biodiesel 1.0 hr + Oil 4 hr | 9.5 |
| Biodiesel 1.5 hr + Oil 4 hr | 8.9 |
| Biodiesel 2.0 hr + Oil 4 gr | 9.1 |
| Biodiesel 1.0 hr + Oil overnight | 11.1 |
| Hexane 1.0 hr + Oil overnight | 3.5 |
| Iso-Propanol 1.0 hr + Oil 1.0 hr | 16.8 |
| 2-Butanol 1.0 hr + Oil 1.0 hr | 17.6 |
| Tert-Butanol 1.0 hr + Oil 1.0 hr | 17.3 |

EXAMPLE 2

Figure 3:
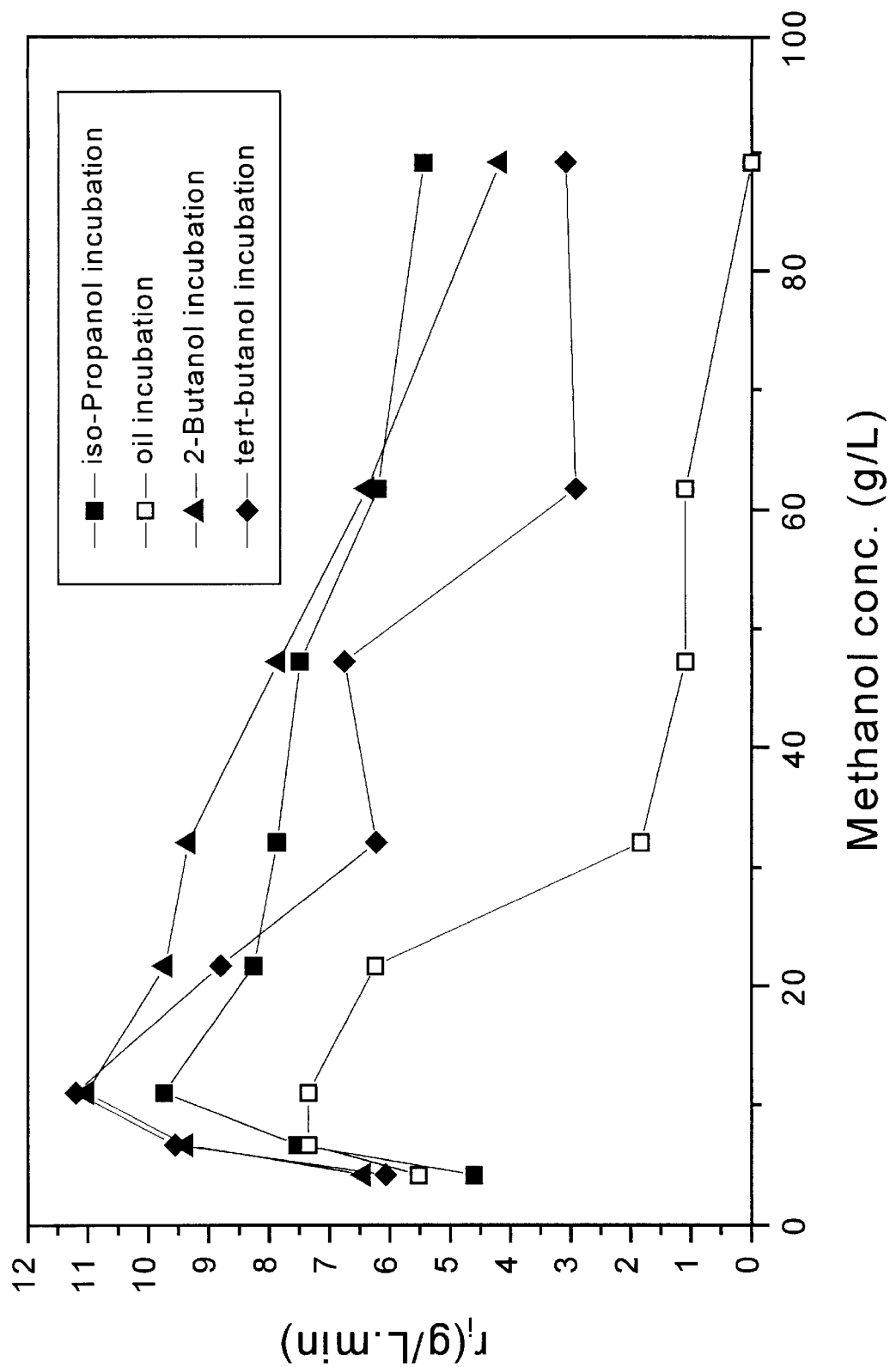
FIG. 3 shows the initial reaction rate of transesterification reaction versus the concentration of methanol, wherein a black square represents an immobilized lipase that has been pretreated by iso-propanol according to the present invention, a hollow square represents a known pretreatment of soybean oil, a triangle represents a pretreatment of 2-butanol according to the present invention, and a rhomboid represents a pretreatment of tert-butanol according to the present invention.

Poisoning of Pretreated Immobilized Lipase by Methanol of Different Concentrations Novozyme 435 pretreated separately with three different non-toxic alcohols and a vegetable oil was added with 5.7 g of a vegetable oil (soybean oil from the Taiwan Sugar Corp.) and methanol at a different mole ratio (oil:methanol=8:1, 5:1, 3:1, 3:2, 1:1, 2:3, 1:2, 1:3), and the reaction was carried out in an incubating chamber at 30° C. under oscillation of 200 rpm for 5 minutes. Upon completion of the reaction, 0.1 g of the sample was taken, and diluted with 10 ml of n-hexane, and then analyzed by HPLC to obtain the contents of methyl ester and unreacted oil. The initial reaction rate of the immobilized lipase was then calculated as the index of the activity of the immobilized lipase. The results are shown in FIG. 3. The initial reaction rate of the immobilized lipase pretreated with a non-toxic alcohol is significantly higher than that of the immobilized lipase immersed only by a vegetable oil, when the methanol concentration increases, as shown in FIG. 3. The immersion of non-toxic alcohol indeed increases the resistance of the immobilized lipase to methanol, wherein iso-propanol and 2-butanol have a better effect.

EXAMPLE 3

Regeneration of the Activity of the Immobilized Lipase that has been Poisoned by Methanol at Different Concentration Novozyme 435 pretreated by immersing with biodiesel 1 hour, washing with soybean oil and then immersing with soybean oil overnight was added with a fixed amount of oil (soybean oil from the Taiwan Sugar Corp.) and then added with various amounts of methanol in different test tubes. The concentration of methanol in the test tubes increased monotonically from mole ratio of oil to methanol=8:1, 5:1, 3:1, 3:2, 1:1, 2:3, 1:2, 1:3, to which experiment numbers (Exp. No.) from 1 to 8 were designated accordingly. The resultant mixtures were oscillated after the test tubes being capped in order to partially or completely deactivate the lipases. The deactivated lipases were subjected to the following washing operations to see whether the activity could be resumed.

Washing operation 1: Washing with soybean oil for three times, and immersing in soybean oil in an incubating chamber at 30° C. overnight.

Washing operation 2: Washing with iso-propanol for three times, washing off iso-propanol with soybean oil, and immersing in soybean oil in an incubating chamber at 30° C. overnight.

Washing operation 3: After being subjected to the washing operation 2, deactivating the lipase in the reaction at an optimum concentration of methanol, and then subjecting the deactivated lipase to the washing operation 2 again.

Figure 4:
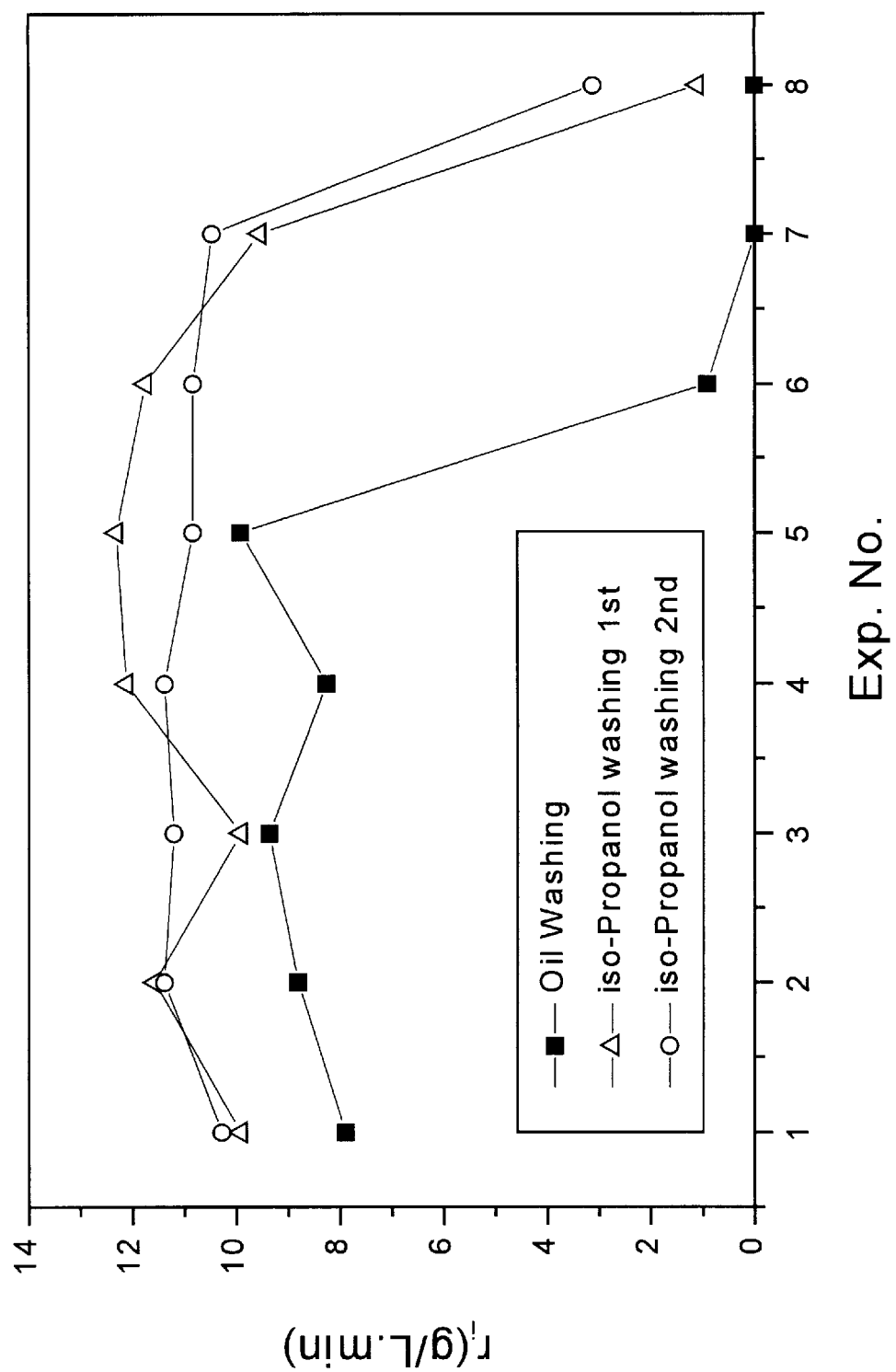
FIG. 4 shows the initial transesterification reaction rates, at the optimum concentration of methanol, of regenerated immobilized lipases by washing with soybean oil (black square dot), or by washing once (triangle dot) or twice (hollow circle dot) with iso-propanol according to the present invention, wherein the experiment numbers (Exp. No.) 1 to 8 on the abscissa respectively represent the mole ratio of oil to methanol (8:1, 5:1, 3:1, 3:2, 1:1, 2:3, 1:2, 1:3, respectively) in the transesterification reactions where immobilized lipases were deactivated.

Then, the activities of the lipases after being subjected to the washing operations were evaluated by repeating the procedures in Example 2, except that an optimum concentration of methanol was used (oil to methanol=3:1). The results are shown in FIG. 4. As shown in FIG. 4, the activities of the lipases after being subjected to the washing operation 1 (washing with soybean oil) nearly disappear for the lipases deactivated in Exp. Nos. 6 to 8 cases where the number of moles of methanol added exceeds that of soybean oil, i.e. black squares at Exp. Nos. 6, 7 and 8. After being washed with iso-propanol (the washing operation 2), the activities of the regenerated immobilized lipases for the Exp. No. 6 and No. 7 cases are increased significantly nearly to a level prior to being poisoned. This demonstrated that washing with a non-toxic alcohol can effectively regenerate a deactivated lipase. Although the recovery of the activity of the regenerated lipase by the washing operation 2 for the Exp. No. 8 case is not satisfactory, the data show that the lipases after being subjected to the washing operation 3 (washing with iso-propanol twice) will once again increase the activity of the lipase. This indicates that the degree of washing with iso-propanol has a positive effect on the recovery of the activity. The optimization of the washing time and the washing temperature should be able to further increase the activity of the lipase. Besides iso-propanol, other experiments according to the present invention also demonstrated that 2-butanol and tert-butanol also have the same effect of regenerating a deactivated immobilized lipase.

Although the present invention has been described with reference to specific details of certain embodiments thereof, it is not intended that such details should be regarded as limitations upon the scope of the invention except as and to the extent that they are included in the accompanying claims. Many modifications and variations are possible in light of the above disclosure.

What is claimed is:

1. A method of preparing a $C_1$–$C_3$ alkyl ester of a fatty acid by transesterification or esterification of a fatty acid glyceride or a free fatty acid with a $C_1$–$C_3$ alcohol, characterized in that a pretreated immobilized lipase is used to catalyze the transesterification or esterification, wherein said pretreated immobilized lipase is prepared by immersing an immobilized lipase in an alcohol having a carbon atom number not less than 3 for a period of time.

2. The method as claimed in claim 1, wherein said alcohol having a carbon atom number not less than 3 has a carbon atom number of 3–8.

3. The method as claimed in claim 2, wherein said alcohol having a carbon atom number not less than 3 has a carbon atom number of 3 or 4.

4. The method as claimed in claim 3, wherein said alcohol having a carbon atom number not less than 3 is 1-propanol, iso-propanol, 1-butanol, 2-butanol, iso-butanol or tert-butanol.

5. The method as claimed in claim 1, wherein said period of time is 0.5–48 hours.

6. The method as claimed in claim 5, wherein said period of time is 0.5–1.5 hours.

7. The method as claimed in claim 1, wherein said pretreated immobilized lipase is prepared by further immersing said immobilized lipase in a vegetable oil for 0.5–48 hours after removing said immobilized lipase from said alcohol having a carbon atom number not less than 3.

8. The method as claimed in claim 1, wherein said immobilized lipase is immobilized on a porous support.

9. The method as claimed in claim 1, wherein said immobilized lipase is from Pseudomanas or Candida.

10. The method as claimed in claim 1, wherein said immobilized lipase is fresh or deactivated.

11. The method as claimed in claim 10, wherein said immobilized lipase is a deactivated immobilized lipase, and said pretreated immobilized lipase is prepared by washing said deactivated immobilized lipase with the alcohol having a carbon atom number not less than 3.

12. The method as claimed in claim 11, wherein said pretreated immobilized lipase is prepared by further immersing said deactivated immobilized lipase in a vegetable oil for 0.5–48 hours after washing said deactivated immobilized lipase with said alcohol having a carbon atom number not less than 3.

13. The method as claimed in claim 1, wherein said $C_1$–$C_3$ alkyl ester is prepared by transesterification of said fatty acid glyceride and said $C_1$–$C_3$ alcohol.

14. The method as claimed in claim 13, wherein said $C_1$–$C_3$ alkyl ester is methyl ester, and said methyl ester is prepared by the transesterification of methanol and an oil or grease comprising a triglyceride.

15. The method as claimed in claim 14, wherein the oil or grease is a vegetable oil.

16. The method as claimed in claim 1, wherein said $C_1$–$C_3$ alkyl ester is prepared by transesterification of said fatty acid glyceride and said $C_1$–$C_3$ alcohol, and the esterification of said free fatty acid and said $C_1$–$C_3$ alcohol.

17. The method as claimed in claim 16, wherein said $C_1$–$C_3$ alkyl ester is methyl ester, and said methyl ester is prepared by the transesterification and esterification of methanol and an oil or grease comprising a glyceride and a free fatty acid.

18. The method as claimed in claim 17, wherein said oil or grease is a vegetable oil, an animal grease, a recycled rendered feedstock oils, or a rendered oil or grease generated during the refining of feedstock oils.

* * * * *